United States Patent
Gong et al.

(10) Patent No.: US 12,266,097 B2
(45) Date of Patent: Apr. 1, 2025

(54) IMAGE ANALYSIS METHOD BASED ON ULTRASOUND IMAGING DEVICE, AND ULTRASOUND IMAGING DEVICE

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventors: Xuehao Gong, Shenzhen (CN); Shuo Liu, Shenzhen (CN); Lei Zhu, Shenzhen (CN); Zhijie Chen, Shenzhen (CN); Juan Yuan, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 790 days.

(21) Appl. No.: 17/112,948

(22) Filed: Dec. 4, 2020

(65) Prior Publication Data
US 2021/0090254 A1    Mar. 25, 2021

Related U.S. Application Data

(63) Continuation of application No. PCT/CN2018/090228, filed on Jun. 7, 2018.

(51) Int. Cl.
*G06T 7/00* (2017.01)
*G16H 30/20* (2018.01)
*G16H 50/20* (2018.01)

(52) U.S. Cl.
CPC ........... *G06T 7/0012* (2013.01); *G16H 30/20* (2018.01); *G16H 50/20* (2018.01); *G06T 2207/10132* (2013.01); *G06T 2207/30096* (2013.01)

(58) Field of Classification Search
CPC ......... G06T 7/0012; G06T 2207/10132; G06T 2207/30096; G06T 2200/24;
(Continued)

(56) References Cited

U.S. PATENT DOCUMENTS 7,783,094 B2    8/2010  Collins et al.
8,900,147 B2 *  12/2014 Yoo ........................ A61B 8/00
                                                       600/407
(Continued)

FOREIGN PATENT DOCUMENTS

CN    1748217 A    3/2006
CN    101011266 A  8/2007
(Continued)

OTHER PUBLICATIONS

PCT International Search Report and the Written Opinion mailed Mar. 11, 2019, issued in related International Application No. PCT/CN2018/090228, with partial English translation (13 pages).
(Continued)

*Primary Examiner* — Santiago Garcia
(74) *Attorney, Agent, or Firm* — Sheppard Mullin Richter & Hampton LLP

(57) ABSTRACT

Image analysis methods based on an ultrasound imaging device and ultrasound imaging devices are provided. An image analysis method may include: obtaining an image of a first section of a target object; generating a first analysis result corresponding to the target object according to the image of the first section; obtaining an image of a second section of the target object; generating a second analysis result corresponding to the target object according to the image of the second section; generating a diagnostic analysis result of the target object according to the first analysis result and the second analysis result; and displaying the diagnostic analysis result of the target object.

13 Claims, 9 Drawing Sheets

(58) Field of Classification Search
CPC .... G06T 2207/10136; G06T 2207/20108; G16H 30/20; G16H 50/20; G16H 30/40; A61B 8/08
See application file for complete search history.

(56) References Cited

U.S. PATENT DOCUMENTS

| | | | |
|---|---|---|---|
| 9,792,681 B2 | 10/2017 | Bryan et al. | |
| 10,349,918 B2* | 7/2019 | Lee | G01S 7/52073 |
| 10,959,702 B2* | 3/2021 | Nouri | G06V 40/67 |
| 11,636,340 B2* | 4/2023 | Liu | G06F 18/25 |
| | | | 382/128 |
| 2001/0024516 A1* | 9/2001 | Yoshioka | G01S 7/52073 |
| | | | 382/128 |
| 2004/0122787 A1 | 6/2004 | Avinash et al. | |
| 2006/0072808 A1* | 4/2006 | Grimm | G06T 7/33 |
| | | | 382/151 |
| 2009/0299191 A1* | 12/2009 | Hyun | A61B 8/08 |
| | | | 600/458 |
| 2009/0306505 A1* | 12/2009 | Yoshikawa | A61B 5/7475 |
| | | | 600/443 |
| 2011/0142319 A1* | 6/2011 | Lee | A61B 8/483 |
| | | | 382/131 |
| 2012/0259555 A1* | 10/2012 | Neville | G01N 33/57434 |
| | | | 702/19 |
| 2014/0005545 A1* | 1/2014 | Lee | A61B 8/467 |
| | | | 600/440 |
| 2014/0241606 A1* | 8/2014 | Park | G06T 7/11 |
| | | | 382/131 |
| 2014/0378836 A1* | 12/2014 | Lee | G06T 7/0014 |
| | | | 600/443 |
| 2015/0164481 A1 | 6/2015 | Lee et al. | |
| 2016/0302759 A1* | 10/2016 | Shi | A61B 8/52 |
| 2018/0211392 A1 | 7/2018 | Kim et al. | |
| 2020/0239937 A1* | 7/2020 | Lee | C12Q 1/6813 |

FOREIGN PATENT DOCUMENTS

| | | |
|---|---|---|
| CN | 101203170 A | 6/2008 |
| CN | 100448409 C | 1/2009 |
| CN | 101904754 A | 12/2010 |
| CN | 104706381 A | 6/2015 |
| CN | 105359161 A | 2/2016 |
| CN | 105361908 A | 3/2016 |
| CN | 105389813 A | 3/2016 |
| CN | 105701331 A | 6/2016 |
| CN | 107680678 A | 2/2018 |
| EP | 3005946 A1 | 4/2016 |

OTHER PUBLICATIONS

First Search dated Sep. 2, 2020, issued in related Chinese Application No. 201880008149.0 (2 pages).
First Office Action dated Sep. 10, 2020, issued in related Chinese Application No. 201880008149.0, with English machine translation (30 pages).
PCT International Preliminary Report on Patentability mailed Dec. 17, 2020, issued in related International Application No. PCT/CN2018/090228, with English translation (14 pages).
Supplementary Search dated Dec. 28, 2020, issued in related Chinese Application No. 201880008149.0 (1 page).
Second Office Action dated Dec. 28, 2020, issued in related Chinese Application No. 201880008149.0 (14 pages).
Bin Liu, "Multi-view based computer-aided detection and Diagnosis scheme for breast masses", A Thesis Submitted in Partial Fulfillment of the Requirements for the Degree of Master of Science, Hauzhong University of Science and Technology, Wuhan, China, May 2009, with English language abstract.

* cited by examiner

IMAGE ANALYSIS METHOD BASED ON ULTRASOUND IMAGING DEVICE, AND ULTRASOUND IMAGING DEVICE

CROSS-REFERENCE TO RELATED APPLICATION

This application is a continuation application of International Patent Application No. PCT/CN2018/090228, filed with the China National Intellectual Property Administration (CNIPA) of People's Republic of China on Jun. 7, 2018, and entitled "IMAGING ANALYSIS METHOD BASED ON ULTRASONIC IMAGING DEVICE, AND ULTRASONIC IMAGING DEVICE". The entire content of the above-identified application is incorporated herein by its reference.

TECHNICAL FIELD

The present disclosure relates to ultrasound imaging, in particular to image analysis methods based on ultrasound imaging device and ultrasound imaging devices.

BACKGROUND

With the development of artificial intelligence technology, the computer aided diagnosis (CAD) software is increasingly used in ultrasound imaging device. The CAD software using artificial intelligence technology can train its own deep neural network through the learning of big data samples, so as to realize the intelligent recognition and intelligent diagnosis of the diseased area in the image, that is, the auxiliary diagnosis function.

Currently, the CAD software usually analyzes a single frame of image and gives diagnostic opinions (such as the location and nature of the lesion area, etc.). In the actual clinical process, the doctor needs to perform a complete scan of the target organ and the diseased area and observe and analyze the section images (such as the longitudinal section image, the transverse section image, or typical feature section image, etc.), so as to obtain the final diagnosis according to the information of multiple section images.

However, the existing CAD software can only directly give the auxiliary diagnosis opinion based on one frame of image, which does not conform to the clinical objective laws and the doctor's operating habits. Therefore, the final diagnosis opinion obtained cannot be convincing.

SUMMARY

The embodiments of the present disclosure provide image analysis methods based on ultrasound imaging device, and ultrasound imaging devices. The ultrasound imaging devices can generate the diagnostic analysis results according to multiple frames of section images, thereby improving the accuracy of the auxiliary diagnosis and the compliance with the clinical objective laws.

In one embodiment, an image analysis method based on ultrasound imaging device is provided, which may include:
  obtaining an image of a first section of a target object;
  generating a first analysis result corresponding to the target object according to the image of the first section;
  obtaining an image of a second section of the target object;
  generating a second analysis result corresponding to the target object according to the image of the second section;
  generating a diagnostic analysis result of the target object according to the first analysis result and the second analysis result; and
  displaying the diagnostic analysis result of the target object.

In one embodiment, an image analysis method based on ultrasound imaging device is provided, which may include:
  obtaining a three-dimensional data of a target object;
  determining an image of a first section and an image of a second section of the target object according to the three-dimensional data of the target object;
  generating a first analysis result corresponding to the target object according to the image of the first section, and generating a second analysis result corresponding to the target object according to the image of the second section;
  generating a diagnostic analysis result of the target object according to the first analysis result and the second analysis result; and
  displaying the diagnostic analysis result of the target object.

In one embodiment, an image analysis method based on ultrasound imaging device is provided, which may include:
  transmitting ultrasound waves to a target object;
  receiving ultrasound echoes of the ultrasound waves returned from the target object to obtain ultrasound echo signals;
  generating images of at least two sections of the target object according to the ultrasound echo signals; and
  generating a diagnosis analysis result of the target object according to the images of the at least two sections.

In one embodiment, an ultrasound imaging device is provided, which may include:
  a probe;
  a transmitting circuit configured to excite the probe to transmit ultrasound waves to a target object;
  a receiving circuit configured to receive, through the probe, ultrasound echoes returned from the target to obtain ultrasound echo signals;
  a processor configured to process the ultrasound echo signals to obtain an ultrasound image of the target object; and
  a display configured to display the ultrasound image.
  Wherein the processor is further configured to:
  obtain an image of a first section of the target object;
  generating a first analysis result corresponding to the target object according to the image of the first section;
  obtaining an image of a second section of the target object;
  generating a second analysis result corresponding to the target object according to the image of the second section;
  generating a diagnostic analysis result of the target object according to the first analysis result and the second analysis result; and
  displaying the diagnostic analysis result of the target object.

In one embodiment, an ultrasound imaging device is provided, which may include:
  a probe;
  a transmitting circuit configured to excite the probe to transmit ultrasound waves to a target object;
  a receiving circuit configured to receive ultrasound echoes returned from the target object through the probe to obtain ultrasound echo signals;

a processor configured to process the ultrasound echo signals to obtain an ultrasound image of the target object; and a display configured to display the ultrasound image.

Wherein the processor is further configured to:

obtain a three-dimensional data of the target object;

determine an image of a first section and an image of a second section of the target object according to the three-dimensional data of the target object;

generate a first analysis result corresponding to the target object according to the image of the first section, and generate a second analysis result corresponding to the target object according to the image of the second section;

generate a diagnostic analysis result of the target object according to the first analysis result and the second analysis result; and display the diagnostic analysis result of the target object.

In one embodiment, an ultrasound imaging device is provided, which may include:

a probe;

a transmitting circuit configured to excite the probe to transmit ultrasound waves to a target object;

a receiving circuit configured to receive ultrasound echoes returned from the target object through the probe to obtain ultrasound echo signals;

a processor configured to process the ultrasound echo signals to obtain an ultrasound image of the target object; and a display configured to display the ultrasound image.

Wherein the processor is further configured to:

transmit the ultrasound waves to the target object;

receive the ultrasound echoes of the ultrasound waves returned from the target object to obtain the ultrasound echo signals;

generate images of at least two sections of the target object according to the ultrasound echo signals; and generate a diagnosis analysis result of the target object according to the images of the at least two sections.

In the embodiments above, the image analysis methods based on ultrasound imaging device are provided. In the methods, the ultrasound imaging device may obtain the image of the first section of the target object and generate the first analysis result corresponding to the target object according to the image of the first section, and may obtain the image of the second section of the target object and generate the second analysis result corresponding to the target object according to the image of the second section. Thereafter, the ultrasound imaging device may generate the diagnostic analysis result of the target object according to the first analysis result and the second analysis result, and display the diagnostic analysis result of the target object. This way, the ultrasound imaging device can generate the diagnostic analysis result according to the images of multiple sections, thereby improving the accuracy of the auxiliary diagnosis and the compliance with the clinical objective laws.

DETAILED DESCRIPTION

The technical solutions in the embodiments of the present disclosure will be clearly and completely described below in conjunction with the drawings. Obviously, the described embodiments are only a part, but not all, of the embodiments of the present disclosure.

The terms "first", "second", "third", "fourth", etc. (if any) in the specification, claims and drawings of the present disclosure are used to distinguish similar objects, but not to describe a specific order or sequence. It should be understood that the data used in this way can be interchanged under appropriate circumstances so that the embodiments described herein can be implemented in an order other than the order illustrated or described herein. In addition, the terms "including" and "having" and any variations thereof are intended to mean non-exclusive inclusion. For example, a process, method, system, product or device that includes a series of steps or units is not necessarily limited to the clearly listed steps or units, but may include other steps or units that are not clearly listed or are inherent to the process, method, product or device.

Figure 1:
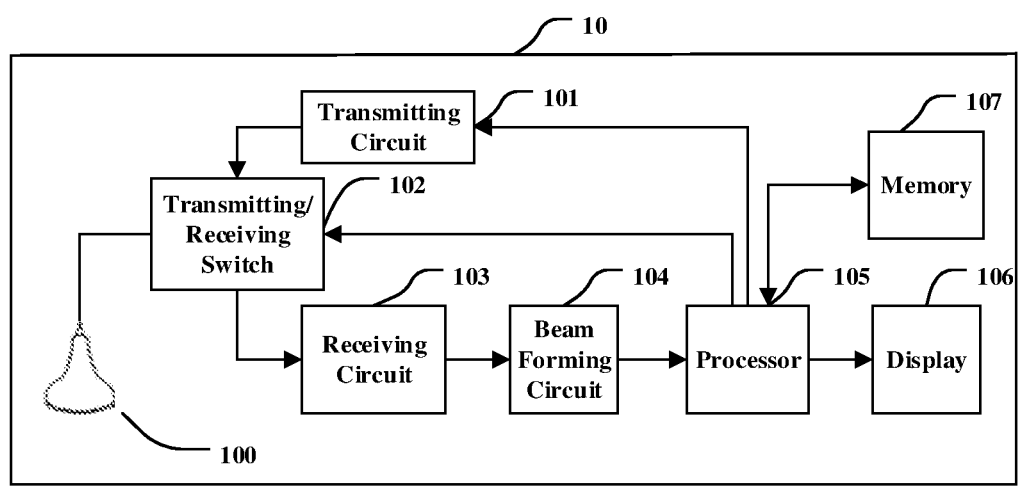
FIG. 1 is a schematic block diagram of an ultrasound imaging device in one embodiment of the present disclosure.

FIG. 1 is a schematic block diagram of an ultrasound imaging device 10 in one embodiment of the present disclosure. The ultrasound imaging device 10 may include a probe 100, a transmitting circuit 101, a transmitting/receiving switch 102, a receiving circuit 103, a beam forming circuit 104, a processor 105 and a display 106. The transmitting circuit 101 may excite the probe 100 to transmit ultrasound waves to a target object. The receiving circuit 103 may receive the ultrasound echoes returned from the target object through the probe 100 to obtain the ultrasound echo signals. The ultrasound echo signals may be sent to the processor 105 after the beam forming circuit 104 performs the beam-forming processing thereon. The processor 105 may process the ultrasound echo signals to obtain an ultrasound image of the target object. The ultrasound image obtained by the processor 105 may be stored in the memory 107. The ultrasound image may be displayed on the display 106.

In the embodiments of the present disclosure, the display 106 of the ultrasound imaging device 10 may be a touch screen, a liquid crystal display, etc., or may be an independent display device such as a liquid crystal display, a television or the like independent of the ultrasound imaging device 10, or may be the display screen on an electronic device such as a mobile phone or a tablet, etc.

In the embodiments of the present disclosure, the memory 107 of the ultrasound imaging device 10 may be a flash memory card, a solid-state memory, a hard disk, or the like.

In the embodiments of the present disclosure, a computer-readable storage medium may also be provided, which may store multiple program instructions. After the multiple program instructions are called and executed by the processor 105, a part or all or any combination of the steps of the imaging methods in the embodiments of the present disclosure may be achieved.

In one embodiment, the computer-readable storage medium may be the memory 107, which may be a non-volatile storage medium such as a flash memory card, a solid-state memory, a hard disk, or the like.

In the embodiments of the present disclosure, the processor 105 of the ultrasound imaging device 10 may be implemented by software, hardware, firmware or a combination thereof, and may use circuits, single or multiple application specific integrated circuits (ASIC), single or multiple general-purpose integrated circuits, single or multiple microprocessors, single or multiple programmable logic devices, a combination of the foregoing circuits or devices, or other suitable circuits or devices, such that the processor 105 can perform the steps of the shear wave elasticity imaging methods in the embodiments.

Figure 2:
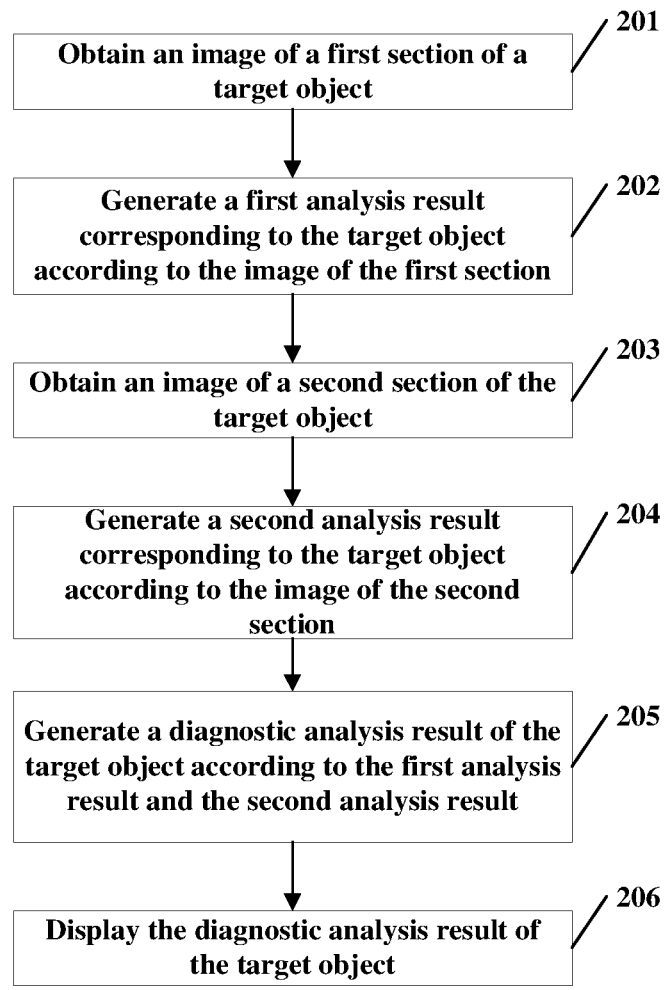
FIG. 2 is a schematic flow chart of an image analysis method based on ultrasound imaging device in one embodiment of the present disclosure.

The image analysis methods based on the ultrasound imaging device in the present disclosure will be described in detail below. Referring to FIG. 2, in one embodiment, an image analysis method based on the ultrasound imaging device is provided, which may be applied to the ultrasound imaging device 10 and be particularly suitable for the ultrasound imaging device 10 including the display 106, and may display the diagnostic analysis result of the target object with the display 106. The ultrasound imaging device 10 may execute instructions. The image analysis method based on the ultrasound imaging device may include the following steps.

In step 201, an image of a first section of the target object may be obtained.

In this embodiment, the ultrasound imaging device may obtain the image of the first section of the target object from a storage device. Alternatively, the ultrasound imaging device may use a probe to scan the target object to obtain the image of the first section. The target object may include, but not limited to, the thyroid, the liver, the pancreas, the kidney or the breast.

In step 202, a first analysis result corresponding to the target object may be generated according to the image of the first section.

In this embodiment, the processor 105 may generate the first analysis result according to the image of the first section.

In step 203, an image of a second section of the target object may be obtained.

In this embodiment, the processor 105 may obtain the image of the second section of the target object from a storage device. Alternatively, the ultrasound imaging device may use the probe 100 to scan the target object to obtain the image of the second section of the target object.

In step 204, a second analysis result corresponding to the target object may be generated according to the image of the second section.

In this embodiment, the processor 105 may generate the second analysis result according to the image of the second section.

In step 205, a diagnostic analysis result of the target object may be generated according to the first analysis result and the second analysis result.

In this embodiment, the processor 105 may generate the diagnostic analysis result of the target object according to both the first analysis result and the second analysis result.

Specifically, the methods for generating the diagnostic analysis result may include, but not limited to, calculating the maximum value, calculating the minimum value, calculating the weighted summation or regression analysis, etc. For example, in the case that the first analysis result is that "the probability of malignant liver nodules is 80%" and the second analysis result is that "the probability of malignant liver nodules is 75%", the diagnostic analysis result obtained by calculating the maximum value may be that "the probability of malignant liver nodules is 80%". For another example, in the case that the first analysis result is that "the probability of benign thyroid nodule is 10%" and the second analysis result is "the probability of benign thyroid nodule is 18%", the diagnostic analysis result obtained by calculating the minimum value may be that "the probability of benign thyroid nodule is 10%".

In step 206, the diagnostic analysis result of the target object may be displayed.

In this embodiment, the diagnostic analysis result of the target object generated by the processor 105 may be displayed on the interface of the display 106.

In the embodiments above, the image analysis methods based on ultrasound imaging device are provided. In the methods, the ultrasound imaging device may obtain the image of the first section of the target object and generate the first analysis result corresponding to the target object according to the image of the first section, and may obtain the image of the second section of the target object and generate the second analysis result corresponding to the target object according to the image of the second section. Thereafter, the ultrasound imaging device may generate the diagnostic analysis result of the target object according to the first analysis result and the second analysis result, and display the diagnostic analysis result of the target object. This way, the ultrasound imaging device can generate the diagnostic analysis result according to the images of multiple sections, thereby improving the accuracy of the auxiliary diagnosis and the compliance with the clinical objective laws.

In one embodiment, in the image analysis method based on ultrasound imaging device, obtaining the image of the first section of the target object may include:
 receiving an instruction for selecting the image of the first section; and
 obtaining the image of the first section of the target object in response to the instruction for selecting the image of the first section.

Obtaining the image of the second section of the target object may include:

receiving an instruction for selecting the image of the second section; and obtaining the image of the second section of the target object responding to the instruction for selecting the image of the second section.

Figure 3:
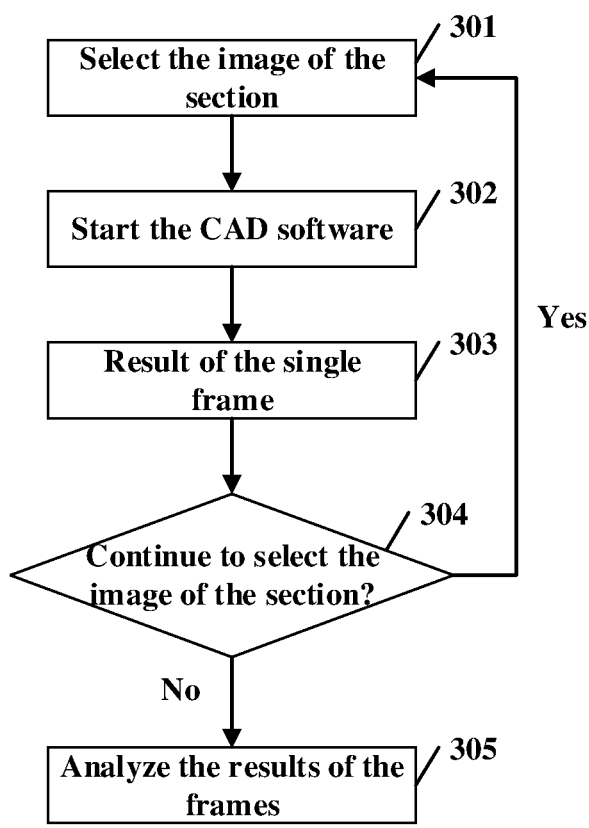
FIG. 3 is a schematic diagram of an operation in an image analysis method based on ultrasound imaging device in one embodiment of the present disclosure.

In this embodiment, the user may manually select the image of section. FIG. 3 is a schematic diagram of an operation in an image analysis method based on ultrasound imaging device in one embodiment of the present disclosure. In the following, the selection of the image of section will be described with reference to FIG. 3.

In step 301, the user may select a certain image of section. For example, when scanning the liver, the user may select a certain image of section according to the angle of the section to be analyzed, thereby triggering the instruction for selecting the image of the first section.

In step 302, in response to the instruction for selecting the image of the first section, the image of the first section may be obtained, and the computer aided diagnosis (CAD) software may be started.

In step 303, an analysis result derived from the single frame of the image of the first section may be obtained by the analysis of the CAD software.

In step 304, it may be determined whether the user desires to select the image of the next section. If it is, the process may be returned to step 301 to select the image of another section with a different angle. That is, the instruction for selecting the image of the second section may be triggered, and in response to the instruction for selecting the image of the second section, the image of the second section may be obtained. The CAD software may be started to obtain the analysis result derived from the single frame of the image of the section. The process may be repeated, until the user no longer select the image of section.

In step 305, the single-frame results corresponding to the images of at least two sections may be used to obtain the diagnosis analysis result.

In the embodiments of the present disclosure, the ultrasound imaging device may also receive an instruction triggered by the user. When the user triggers the instruction for selecting the image of the first section, the image of the first section may be obtained, and when the user triggers the instruction for selecting the image of the second section, the image of the second section may be obtained. This way, the user can manually select the images of at least two sections according to actual requirements. Therefore, the flexibility in selecting the image of section can be increased.

Optionally, in one embodiment, after obtaining the image of the second section of the target object, the image analysis method based on the ultrasound imaging device may further include:

obtaining an image of a third section of the target object; and generating a third analysis result corresponding to the target object according to the image of the third section.

Wherein generating the diagnostic analysis result of the target object according to the first analysis result and the second analysis result may include:

generating the diagnostic analysis result of the target object according to the first analysis result, the second analysis result and the third analysis result.

In this embodiment, if it is desired to obtain the image of the next section after the image of the second section of the target object is obtained, an instruction for selecting the image of the third section may be triggered. In response to the instruction for selecting the image of the third section, the processor 105 may obtain the image of the third section of the target object. The CAD software may be started to analyze the images of the sections to obtain the first analysis result of the image of the first section, the second analysis result of the image of the second section and the third analysis result of the image of the third section, and generate the diagnostic analysis result of the target object according to the first analysis result, the second analysis result and the third analysis result.

Figure 4:
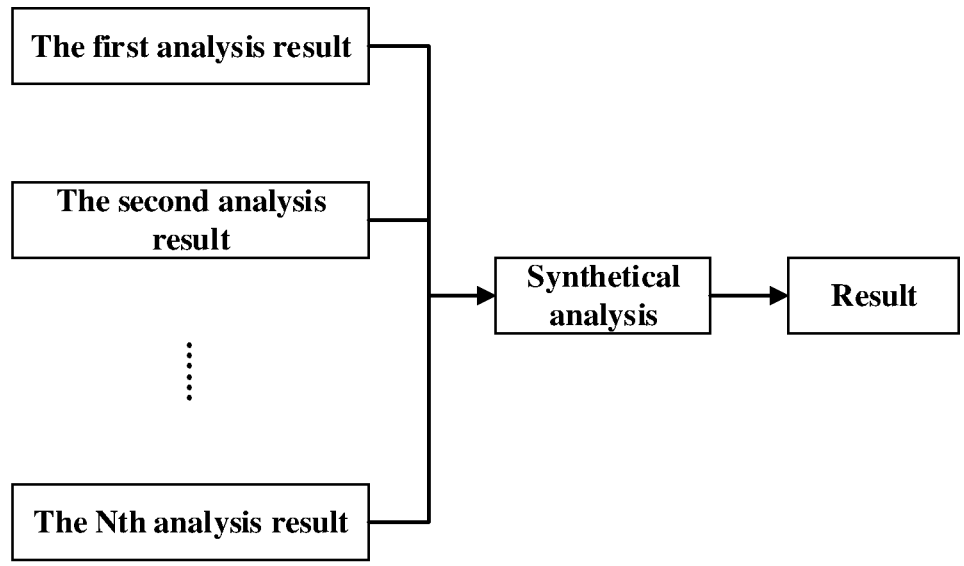
FIG. 4 is a schematic flow chart of an image analysis method based on ultrasound imaging device in one embodiment of the present disclosure.

Specifically, referring to FIG. 4, which is a schematic flow chart of an image analysis method based on the ultrasound imaging device in one embodiment of the present disclosure, the CAD software may be started to analyze the images of the sections to obtain the analysis results of the images of N sections, and generate the final diagnostic analysis result of the target object synthetically according to the analysis results of the images of the N sections. For example, the user may input images of multiple sections of the thyroid, and the CAD software may obtain an extent of disease for the image of each section, and output a final extent of the disease according to the extents of disease obtained based on the images of the multiple sections. The extent of the disease may include the probability of benign or malignant thyroid nodules or TI-RADS, the probability of benign or malignant breast nodules or BI-RADS, fatty liver grade, or the like. For example, the user may input the images of multiple sections of the liver and a fatty liver grade may be obtained for the image of each section, and the CAD software may output a final fatty liver grade synthetically according to the fatty liver grades obtained based on the images of the multiple sections.

Figure 5:
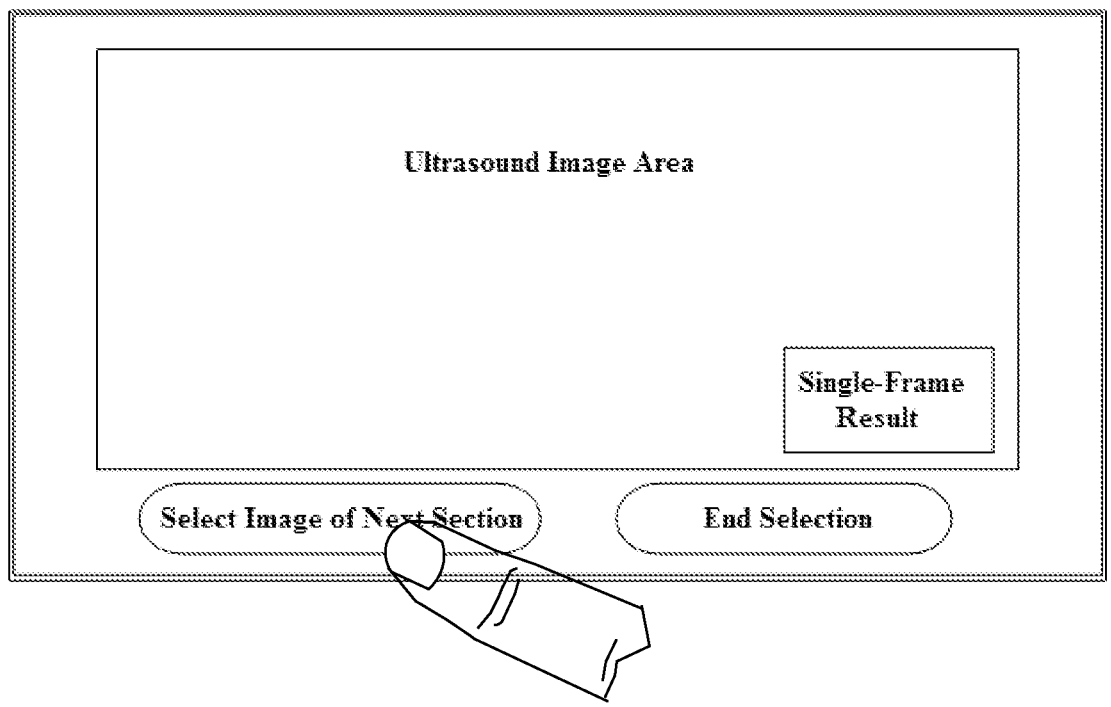
FIG. 5 is a schematic diagram of an interface for triggering a section image selection instruction in an application scenario.

Referring to FIG. 5, which is a schematic diagram of an interface for triggering the instruction for selecting the image of the section, when the user clicks "select image of next section" on the interface on the display 106, the instruction for selecting the image of the section may be triggered.

In the embodiments of the present disclosure, after obtaining the image of the second section of the target object, the ultrasound imaging device may further obtain the image of the third section of the target object and generate the third analysis result corresponding to the target object according to the image of the third section, and finally generate the final diagnostic analysis result of the target object synthetically according to the first analysis result, the second analysis result and the third analysis result. This way, the final diagnostic analysis result can be based on not only the images of two sections, but also the images of more sections according to actual needs, such that the generated final diagnostic analysis result has greater reliability.

In one embodiment, after the instruction for selecting the image of the second section is received, the image analysis method based on the ultrasound imaging device may further include:

receiving an instruction for ending the selection; and in response to the instruction for ending the selection, ending the selection of the image of the section to execute the step of generating the diagnostic analysis result of the target object according to the first analysis result and the second analysis result.

Figure 6:
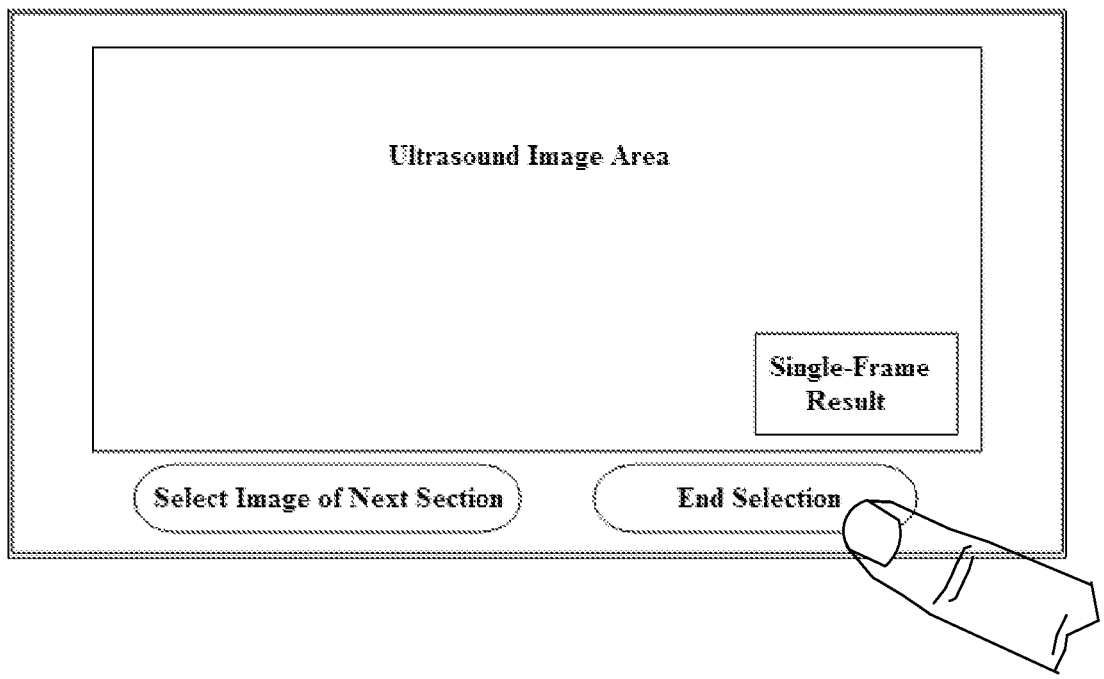
FIG. 6 is a schematic diagram of an interface for triggering an ending image selection instruction in an application scenario.

In the embodiments, in addition to triggering the instruction for selecting the image of the section on the interface of the display 106 of the ultrasound imaging device, the instruction for ending the selection may also be triggered. Referring to FIG. 6 that is a schematic diagram of an interface for triggering the instruction for ending the selection, when the user selects "End Selection", the ultrasound imaging device may perform a synthesized analysis on the analysis results of the images of the sections to generate the final diagnostic analysis result, and display the final diagnostic analysis result.

In the embodiments of the present disclosure, the ultrasound imaging device may receive the instruction for ending the selection, and, in response to the instruction for ending the selection, end the selection of the image of the section, so as to execute the step of generating the diagnostic analysis result of the target object according to the first analysis result and the second analysis result. This way, it is possible to end the selection of the image of the section according to user needs, thereby improving the operability.

In one embodiment, after generating the diagnostic analysis result of the target object according to the first analysis result and the second analysis result, the image analysis method based on the ultrasound imaging device may further include:

receiving a data review instruction; and in response to the data review instruction, displaying the first analysis result and/or the second analysis result.

In this embodiment, after obtaining the diagnostic analysis result of the target object, the ultrasound imaging device may further receive a data review instruction triggered by the user, and, in response to the data review instruction, display the first analysis result or the second analysis result, or display both the first analysis result and the second analysis result.

Figure 7:
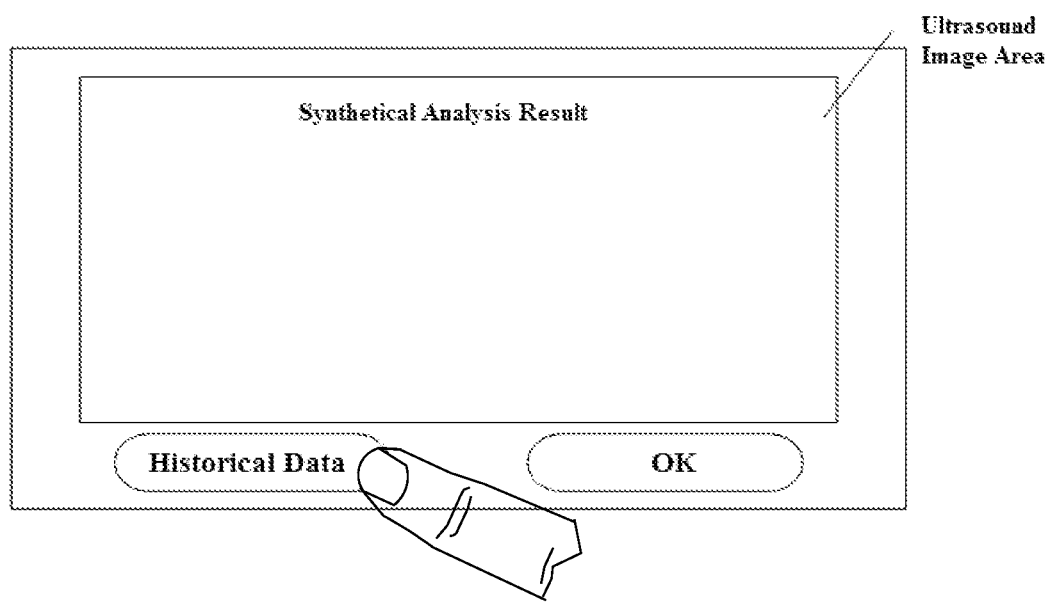
FIG. 7 is a schematic diagram of an interface for triggering a data review instruction in an application scenario.

Referring to FIG. 7 that is a schematic diagram of an interface for triggering the data review instruction in an application scenario of the present disclosure, when the user clicks the "historical data" on the interface of the display 106, the data review instruction may be triggered. The data review instruction may be used to review the analysis results of the images of the sections previously obtained. When the user clicks "OK" on the interface of the display 106, the CAD software may be exited.

In the embodiments of the present disclosure, after generating the diagnostic analysis result of the target object according to the first analysis result and the second analysis result, the ultrasound imaging device may further receive the data review instruction, and display at least one of the first analysis result and the second analysis result in response to the data review instruction. This way, it is convenient for the user to review the analysis result of each image, thereby improving the practicability and convenience.

In one embodiment, in the image analysis method based on the ultrasound imaging device, generating the first analysis result corresponding to the target object according to the image of the first section may include:

performing a computer-aided diagnosis (CAD) analysis on the image of the first section to obtain the first analysis result corresponding to the target object, wherein the first analysis result indicates the extent of disease corresponding to the image of the first section.

Generating the second analysis result corresponding to the target object according to the image of the second section may include:

performing a computer-aided diagnosis (CAD) analysis on the image of the second section to obtain the second analysis result corresponding to the target object, wherein the second analysis result indicates the extent of disease corresponding to the image of the second section.

Figure 8:
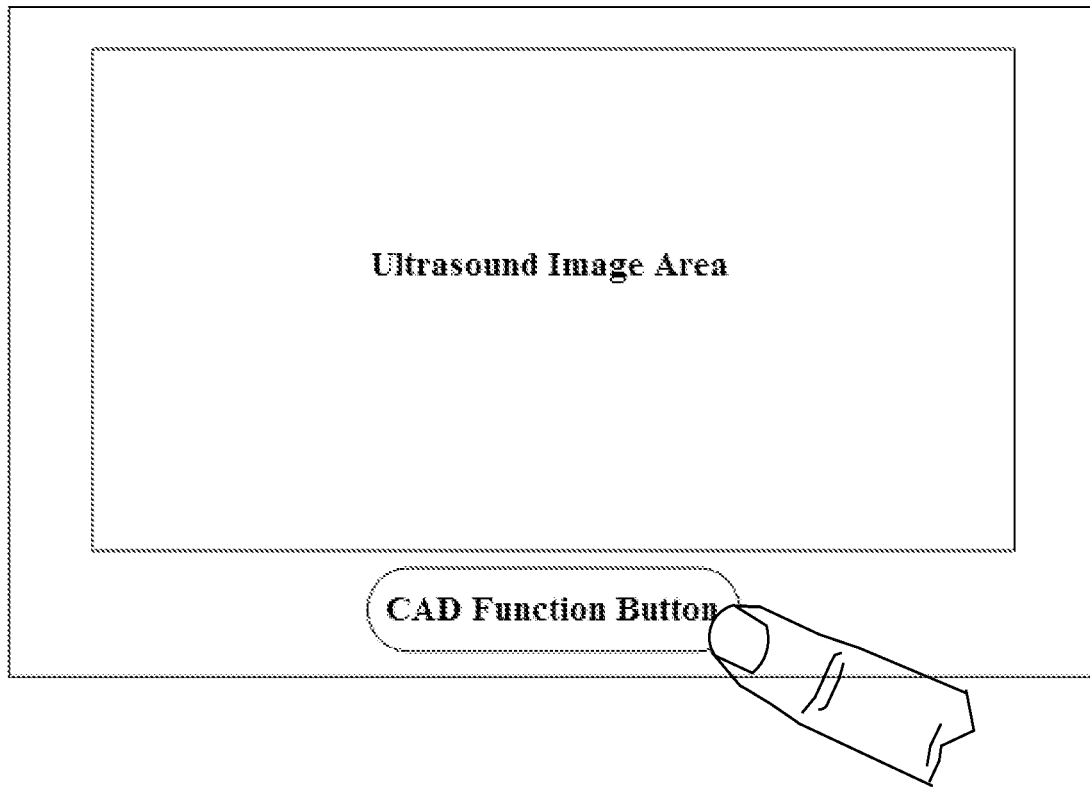
FIG. 8 is a schematic diagram of an interface for triggering the CAD analysis function in an application scenario.

In this embodiment, a common CAD analysis method is described. Referring to FIG. 8 that is a schematic diagram of an interface for triggering the CAD analysis function in an application scenario of the present disclosure, when the user clicks the "CAD function button" on the interface of the display 106, the CAD analysis to the image of the first section may be started to obtain the first analysis result corresponding to the target object. The first analysis result may indicate the extent of disease of the target object that may include probability of benign or malignant thyroid nodules or TI-RADS, probability of benign or malignant breast nodules or BI-RADS, fatty liver grade, or the like. Similarly, when the user continues to click the "CAD function button" on the interface of the display 106, the CAD analysis to the image of the second section may be started to obtain the second analysis result corresponding to the target object. The second analysis result may also indicate the extent of disease of the target object. The extent of disease may include probability of benign or malignant thyroid nodules or TI-RADS, probability of benign or malignant breast nodules or BI-RADS, fatty liver grade, or the like. It can be understood that the CAD function may be implemented by many methods, including but not limited to neural networks, decision trees, support vector machines, Bayesian networks, deep learning, etc., other pattern recognition or machine learning methods, etc.

In the embodiments of the present disclosure, the ultrasound imaging device may perform the computer-aided diagnosis (CAD) analysis on the image of the first section to obtain the first analysis result corresponding to the target object, and perform the CAD analysis on the image of the second section to obtain the second analysis result corresponding to the target object. This way, the CAD analysis can be used to obtain the extent of disease corresponding to the image of the sections, thereby improving the feasibility and operability.

In one embodiment, in the image analysis method based on the ultrasound imaging device, performing the CAD analysis on the image of the first section to obtain the first analysis result corresponding to the target object may include:

extracting the lesion features in the image of the first section;

analyzing the size, density or shape of the lesion features to obtain the first lesion result; and perform a classification processing on the first lesion result to obtain the first analysis result.

Performing the CAD analysis on the image of the second section to obtain the second analysis result corresponding to the target object may include:

extracting the lesion features in the image of the second section;

analyzing the size, density or shape of the lesion features to obtain the second lesion result; and perform a classification processing on the second lesion result to obtain the second analysis result.

In this embodiment, the processor 105 may first extract the lesion features from the normal structures. The purpose of the image processing here is to make it easy for the computer to identify the possible lesions, such that the computer can identify the lesions and suspicious structures from the complex anatomical background. Usually, in this process, the image may first be digitized. For different lesions, different image processing and calculation methods may be used. The basic principle is that the image enhancement and image filtering can be achieved better, such that the computer can separate the suspicious lesions from the normal anatomical background.

The purpose of the image feature extraction is to further quantify the extracted lesion features, that is, it is an analysis and quantification process of the lesion signs. The analyzed signs may be the imaging representations that are valuable for the diagnosis of the lesion, such as the size, density or morphological characteristics of the lesion, etc. This way, the lesion result may be obtained.

The data processing process may be performed. The lesion results obtained in the step above may be input into various mathematical or statistical algorithms such as artificial neuron networks, etc., wherein the lesion results may be classified so as to distinguish the lesions, thereby obtaining the analysis results of the disease.

In the embodiments of the present disclosure, the ultrasound imaging device may obtain the analysis result by extracting the features of the image. That is, the ultrasound imaging device may extract the lesion features in the image of the first section, analyze the size, density or shape of the lesion features to obtain the first lesion result, and classify the first lesion result to obtain the first analysis result. Similarly, the ultrasound imaging device may extract the features in the image of the second section to obtain the second analysis result. This way, by extracting the features in the image of the section to perform the analysis, the reliability of the analysis result can be increased.

In one embodiment, in the image analysis method based on the ultrasound imaging device, generating the first analysis result corresponding to the target object according to the image of the first section may include:
  receive a first result analysis instruction; and
  in response to the first result analysis instruction, generating the first analysis result corresponding to the target object according to the image of the first section and displaying the first analysis result.

Generating the second analysis result corresponding to the target object according to the image of the second section may include:
  receiving a second result analysis instruction; and
  in response to the second result analysis instruction, generating the second analysis result corresponding to the target object according to the image of the second section and displaying the second analysis result.

Figure 9:
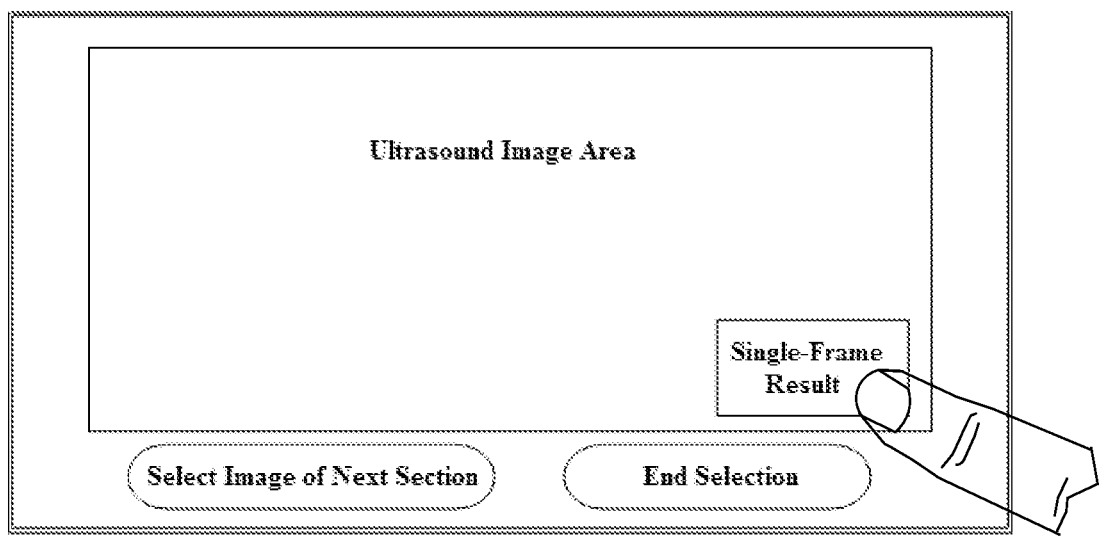
FIG. 9 is a schematic diagram of an interface for triggering the analysis instruction in an application scenario.

In this embodiment, the ultrasound imaging device may not only directly output the final diagnostic analysis result of the target object, but also output the analysis result of a certain frame of image of the section according to the needs of the user. Specifically, referring to FIG. 9 that is a schematic diagram of an interface for triggering the result analysis instruction in an application scenario of the present disclosure, when the user clicks on the "single frame result" on the interface of the display 106, the analysis may be performed on one certain frame of image of the section, and the analysis result of the target object may be displayed.

In the embodiments of the present disclosure, the ultrasound imaging device may receive the first result analysis instruction, and generate and display the first analysis result corresponding to the target object according to the image of the first section. Similarly, the ultrasound imaging device may receive the second result analysis instruction, and generate and display the second analysis result corresponding to the target object according to the image of the second section. This way, the user can review the analysis result of any frame of image of the section, which is convenient for the user to operate, thereby improving the flexibility.

In one embodiment, in the image analysis method based on the ultrasound imaging device, generating the final diagnostic analysis result of the target object according to the first analysis result and the second analysis result may include:

calculating a first result to be processed according to the first analysis result and a first coefficient;
calculating a second result to be processed according to the second analysis result and a second coefficient; and
summing the first result to be processed and the second result to be processed to obtain the diagnostic analysis result of the target object.

In this embodiment, a method for obtaining the diagnosis analysis result using "weighted summation" will be described. First, the first analysis result and the second analysis result may be obtained through the CAD software. Thereafter, the diagnostic analysis result of the target object may be calculated as:

$$Q = A \times a + B \times b$$

Wherein Q represents the diagnostic analysis result, A represents the first analysis result, a represents the first coefficient, B represents the second analysis result, and b represents the second coefficient. For example, assuming A is the cancer possibility of 90%, B is the cancer possibility of 50%, a is 0.8, and b is 0.2, the obtained Q is 82%, that is, the diagnostic analysis result is that the cancer possibility of the target object is 82%.

In the embodiments of the present disclosure, the first result to be processed may be calculated according to the first analysis result and the first coefficient, the second result to be processed may be calculated according to the second analysis result and the second coefficient, and the diagnostic analysis result of the target object may be obtained by summing the first result to be processed and the second result to be processed. This way, by obtaining the diagnosis analysis result through the weighted summation, the unreality of certain data or the like may be eliminated, thereby effectively improving the reliability.

Figure 10:
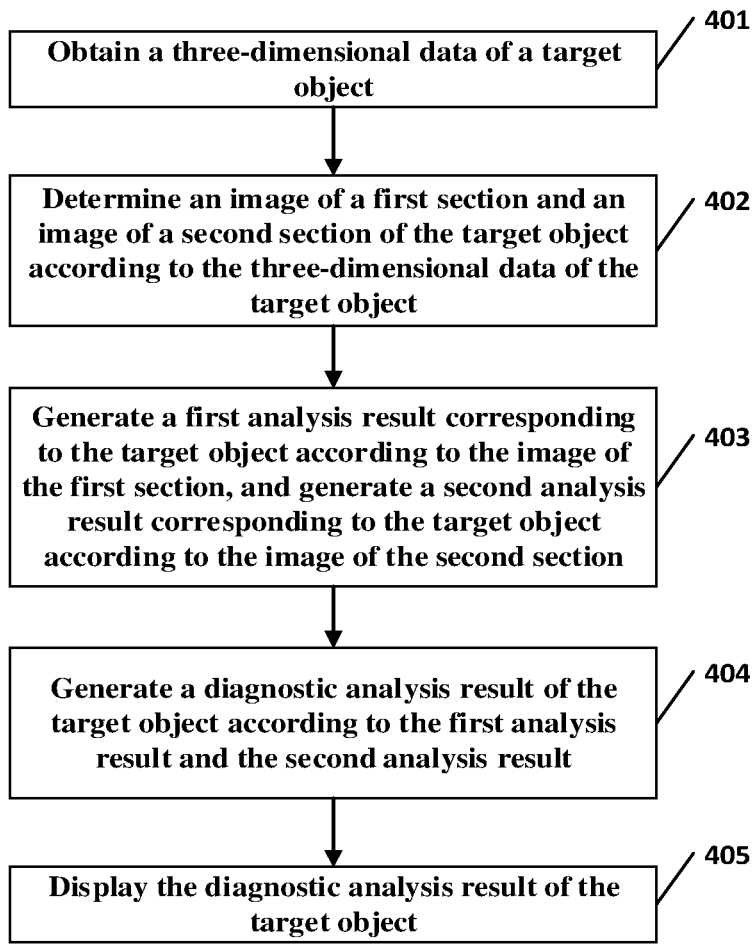
FIG. 10 is a schematic flow chart of an image analysis method based on ultrasound imaging device in another embodiment of the present disclosure.

Another image analysis method based on ultrasound imaging device will be described in detail below. FIG. 10 shows an image analysis method based on ultrasound imaging device in one embodiment, which is applied to the ultrasound imaging device 10, especially suitable for the ultrasound imaging device 10 including the display 106 that may be used to display the diagnostic analysis result of the target object. The ultrasound imaging device 10 may be used to execute corresponding instructions. The image analysis method based on the ultrasound imaging device may include the following steps.

In step 401, the three-dimensional data of the target object may be obtained.

In this embodiment, the processor 105 may first obtain the three-dimensional data of the target object. The target object may include, but not limited to, the thyroid, the liver, the pancreas, the kidney, the breast or the like. The three-dimensional data may allow people to observe the three-dimensional lesions of the organs, and observe the organs and lesions from any angles such as front, back, left, right, top or bottom.

In step 402, the image of the first section and the image of the second section of the target object may be determined according to the three-dimensional data of the target object.

In this embodiment, the CAD software may determine the image of the first section and the image of the second section according to the three-dimensional data of the target object, wherein the image of the first section or the image of the second section may be the image of the standard section or typical characteristic section.

In step 403, the first analysis result corresponding to the target object may be generated according to the image of the first section, and the second analysis result corresponding to the target object may be generated according to the image of the second section.

In this embodiment, the processor 105 may perform the analysis on the image of the first section to obtain the first analysis result of the target object, and perform the analysis on the image of the second section to obtain the second analysis result of the target object.

Specifically, assuming that the three-dimensional data of the breast is obtained through the whole breast scan, the CAD software may automatically obtain the images of the long-axis section, short-axis section and micro-calcification section of the breast nodule, and perform the analysis to obtain the size and lesion nature of the breast nodule according to the images of these sections. Assuming that the three-dimensional data of the heart is acquired through the matrix probe, the CAD software may automatically obtain the images of the apical four-chamber section, the left ventricular long-axis section and the left ventricular short-axis section of the heart, and perform the analysis to obtain the left ventricular volume or other cardiac function parameters and the disease state of the heart according to the images of these sections.

In step 404, the diagnostic analysis result of the target object may be generated according to the first analysis result and the second analysis result.

In this embodiment, the processor 105 may generate the diagnostic analysis result of the target object synthetically according to the first analysis result and the second analysis result.

Specifically, the methods for generating the diagnostic analysis result may include, but not limited to, calculating the maximum value, calculating the minimum value, weighted summation or regression analysis, etc. For example, the first analysis result may be that "the probability of malignant liver nodules is 80%", the second analysis result may be that "the probability of malignant liver nodules is 75%", and the diagnostic analysis result obtained by calculating the maximum value may be that "the probability of malignant liver nodules is 80%. For another example, the first analysis result may be that "the probability of benign thyroid nodule is 10%", the second analysis result may be that "the probability of benign thyroid nodule is 18%", and the diagnostic analysis result obtained by calculating the minimum value may be that "the probability of benign thyroid nodule is 10%".

In step 405, the diagnosis analysis result of the target object may be displayed.

In this embodiment, the diagnostic analysis result of the target object may be displayed on the interface of the display 106 of the ultrasound imaging device.

In the embodiments of the present disclosure, the image analysis methods based on ultrasound imaging device are provided. In the methods, the ultrasound imaging device may obtain the three-dimensional data of the target object, determine the image of the first section and the image of the second section of the target object according to the three-dimensional data of the target object, generate the first analysis result corresponding to the target object according to the image of the first section, generate the second analysis result corresponding to the target object according to the image of the second section, generate the diagnostic analysis result of the target object according to the first analysis result and the second analysis result, and display the diagnostic analysis result of the target object. This way, the ultrasound imaging device can generate the diagnostic analysis result according to the frames of images of multiple 1 sections and the three-dimensional data, thereby improving the accuracy of the auxiliary diagnosis and the compliance with clinical objective laws.

In one embodiment, after determining the image of the first section and the image of the second section of the target object according to the three-dimensional data of the target object, the image analysis method based on the ultrasound imaging device may further include:

determining the image of the third section of the target object according to the three-dimensional data of the target object; and generating a third analysis result corresponding to the target object according to the image of the third section.

Generating the diagnostic analysis result of the target object according to the first analysis result and the second analysis result may include:

generating the diagnostic analysis result of the target object according to the first analysis result, the second analysis result and the third analysis result.

Figure 11:
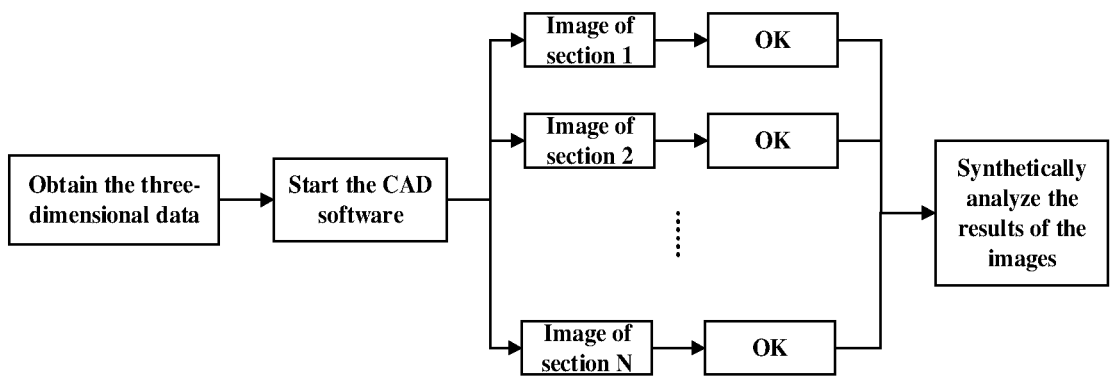
FIG. 11 is a schematic flow chart of an image analysis method based on ultrasound imaging device in another embodiment of the present disclosure.

In this embodiment, the image analysis method based on the ultrasound imaging device will be described with reference to FIG. 11 that is a flow chart of the image analysis method based on the ultrasound imaging device in another embodiment of the present disclosure. As shown in the figure, the three-dimensional data of the target object may be obtained first. Thereafter, the CAD software may be started to analyze the images of the sections using the three-dimensional data to obtain the analysis results of the images of the sections. Assuming that the first analysis result is obtained by analyzing the image of the first section (section image 1) and the second analysis result is obtained by analyzing the image of the second section (section image 2), the final diagnostic analysis result of the target object may be obtained synthetically according to the analysis results of the two section images.

In the embodiments of the present disclosure, after obtaining the image of the second section of the target object, the ultrasound imaging device may further obtain the image of the third section of the target object, generate the third analysis result corresponding to the target object according to the image of the third section, and generate the diagnostic analysis result of the target object according to the first analysis result, the second analysis result and the third analysis result. This way, the diagnostic analysis result may be obtained not only based on two frames of images of the sections, but also based on the images of more sections according to actual needs. Therefore, the generated diagnostic analysis result may have greater reliability.

In one embodiment, in the image analysis method based on the ultrasound imaging device, generating the diagnostic analysis result of the target object according to the first analysis result and the second analysis result may include:

receiving the result analysis instructions; and in response to the result analysis instruction, generating the diagnostic analysis result of the target object according to the first analysis result and the second analysis result.

Figure 12:
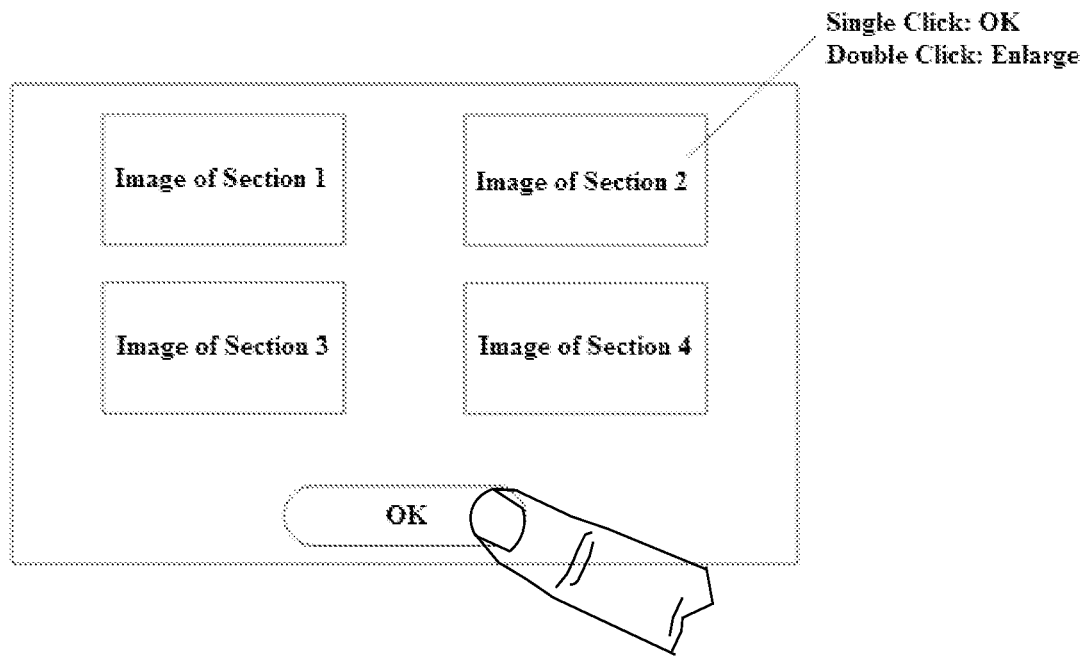
FIG. 12 is a schematic diagram of an interface for triggering the analysis instruction in an application scenario.

In this embodiment, the user may also manually trigger the view of the diagnosis analysis result. Referring to FIG. 12 that is a schematic diagram of an interface for triggering the result analysis instruction in an application scenario of the present disclosure, when the user clicks "OK" on the interface of the display 106, the result analysis instruction may be triggered. At this time, in response to the result analysis instruction, the diagnostic analysis result of the target object may be generated according to the first analysis result and the second analysis result, and be displayed.

In the embodiment of the present disclosure, the ultrasound imaging device may receive the result analysis instruction triggered by the user, and, in response to the result analysis instruction, generate the diagnostic analysis result of the target object according to the first analysis result and the second analysis result. This way, the final diagnostic analysis result can be displayed consistently, thereby increasing the practicability of the solution.

In one embodiment, after the image of the first section and the image of the second section of the target object are determined according to the three-dimensional data of the target object, the image analysis method based on the ultrasound imaging device may further include:
  receiving an image display instructions; and
    in response to the image display instruction, the image of the first section and/or the image of the second section may be enlarged and displayed.

Figure 13:
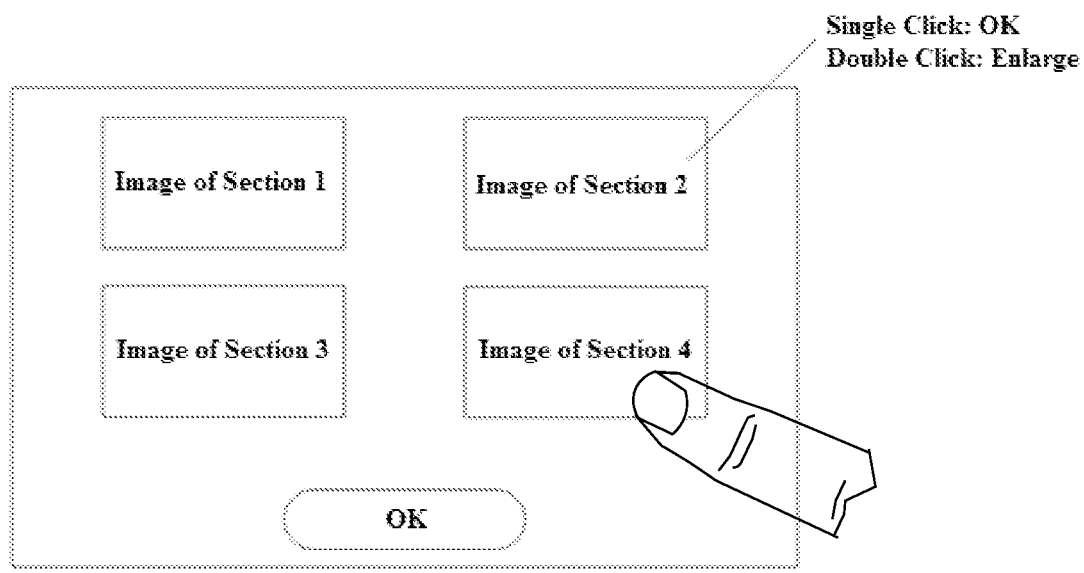
FIG. 13 is a schematic diagram of an interface for triggering the image display instruction in an application scenario.

In this embodiment, after determining the image of the first section and the image of the second section of the target object, the processor 105 may further receive the image display instruction triggered by the user. Referring to FIG. 13 that is a schematic diagram of an interface for triggering the image display instruction in an application scenario of the present disclosure, the CAD software may obtain the images of several standard sections and/or salient feature sections, and the user may select and view at least one section image. One possible implementation is that single-clicking the image means confirming the selection of said image, and double-clicking said image means enlarging for view.

In the embodiments of the present disclosure, the ultrasound imaging device may also receive the image display instruction triggered by the user, and, in response to the image display instruction, magnify and display at least one of the image of the first section and the image of the second section. This way, the user can select the section image that needs to be enlarged. Therefore, it is convenient for the user to view, and the practicability of the solution can be increased.

Figure 14:
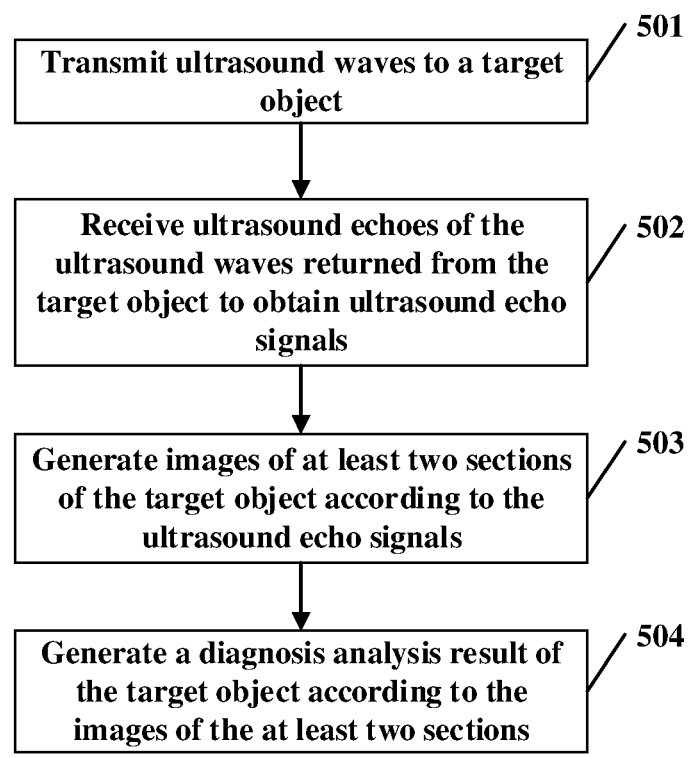
FIG. 14 is a schematic flow chart of an image analysis method based on ultrasound imaging device in another embodiment of the present disclosure.

Another image analysis method based on ultrasound imaging device will be described in detail below. FIG. 14 shows an image analysis method based on ultrasound imaging device in one embodiment, which is applied to the ultrasound imaging device 10, especially suitable for the ultrasound imaging device 10 including the display 106 that may be used to display the diagnostic analysis result of the target object. The ultrasound imaging device 10 may be used to execute corresponding instructions. The image analysis method based on the ultrasound imaging device may include the following steps.

In step 501, the ultrasound waves may be transmitted to the target object.

In this embodiment, the transmitting circuit 101 may transmit through the probe the ultrasound waves to the target object. The target object may include, but not limited to, the thyroid, the liver, the pancreas, the kidney or the breast.

In step 502, the ultrasound echoes of the ultrasound waves returned from the target object may be received to obtain the ultrasound echo signals.

In this embodiment, the processor 105 may receive through the probe the ultrasound echoes of the ultrasound waves returned from the target object to obtain the ultrasound echo signals.

In step 503, the images of at least two sections of the target object may be generated according to the ultrasound echo signals.

In this embodiment, the processor 105 may obtain the images of at least two sections. The images of the sections may be the images of standard sections or typical characteristics sections.

In step 504, the diagnosis analysis result of the target object may be generated according to the images of the at least two sections.

In this embodiment, the processor 105 may respectively perform the analysis on the images of the at least two sections to obtain the analysis result corresponding to the image of each section, and obtain the diagnostic analysis result of the target object according to the analysis results of the images of the at least two sections.

In the embodiments, the image analysis methods based on the ultrasound imaging device are provided. In the methods, the ultrasound imaging device may transmit the ultrasound waves to the target object, receive the ultrasound echoes of the ultrasound waves returning from the target object to obtain the ultrasound echo signals, generate the images of at least two sections of the target object according to the ultrasound echo signals, and generate the diagnostic analysis result of the target object according to the images of the at least two sections. This way, the ultrasound imaging device can generate the diagnostic analysis result according to the images of multiple sections, thereby improving the accuracy of the auxiliary diagnosis and the compliance with clinical objective laws.

In one embodiment, in the image analysis method based on the ultrasound imaging device, generating the images of the at least two sections according to the ultrasound echo signals may include:
  obtaining the image of the first section of the target object;
  generating the first analysis result corresponding to the target object according to the image of the first section;
  obtaining the image of the second section of the target object; and
  generating the second analysis result corresponding to the target object according to the image of the second section.

Generating the diagnostic analysis result of the target object according to the images of the at least two sections may include:
  generating the diagnostic analysis result of the target object according to the first analysis result and the second analysis result.

In this embodiment, the processor 105 may obtain the image of the first section of the target object first. The image of the first section of the target object may obtained from the local storage device, or be obtained by scanning the target object with the probe 100 of the ultrasound imaging device. The CAD software may be used to analyze the image of the first section to obtain the first analysis result of the target object. Similarly, the ultrasound imaging device may obtain the image of the second section from the local storage device, or by scanning the target object with the probe 100 thereof. The CAD software may be used to analyze the image of the second section to obtain the second analysis result of the target object. Finally, the desired diagnostic analysis result may be obtained according to both the first analysis result and the second analysis result.

In the embodiments of the present disclosure, the ultrasound imaging device may automatically obtain the images of multiple sections, analyze the image of each section to obtain the analysis results corresponding to the target object respectively, and obtain the final diagnosis analysis result synthetically according to the analysis results. This way, the ultrasound imaging device can directly output the final diagnostic analysis result according to the images of the multiple sections without displaying the analysis result frame by frame, thereby improving the practicability of the solution.

The embodiments above may be implemented entirely or partly by software, hardware, firmware or any combination thereof. When implemented by software, they can be implemented entirely or partly in the form of a computer program product.

The computer program product may include one or more computer instructions. When the computer instructions are loaded and executed in the computer, the processes or functions described in the embodiments of the present disclosure may be generated in whole or in part. The computer may be a general-purpose computer, a special-purpose computer, a computer network, or other programmable devices. The computer instructions may be stored in a computer-readable storage medium, or be transmitted from one computer-readable storage medium to another computer-readable storage medium. For example, the computer instructions may be transmitted from a website, computer, server or data center to another website, computer, server or data center via wired (such as coaxial cable, optical fiber, Digital Subscriber Line (DSL)) or wireless (such as infrared, wireless, microwave, etc.) connection. The computer-readable storage medium may be any available medium that can be used for storing by a computer or a data storage device such as an integrated server or data center which include one or more available media. The available medium may be a magnetic medium (such as a floppy disk, a hard disk, a magnetic tape), an optical medium (such as a DVD), a semiconductor medium (such as a solid state hard disk (SSD) or the like.

Those skilled in the art can clearly understand that, regarding the specific working process of the system, device and unit described above, reference may be made to the corresponding processes in the methods described above, which, for the convenience and conciseness of the description, will not be repeated here.

It should be understood that in the embodiments of the present disclosure the disclosed systems, devices and methods may be implemented in other ways. For example, the devices described above are only illustrative. For example, the division of the units is only a logical function division, and there may be other divisions in actual implementation. For example, multiple units or components may be combined or be integrated into another system. Some features may be ignored or not implemented. In addition, the displayed or discussed mutual coupling or direct coupling or communication connection may be indirect coupling or communication connection through some interfaces, devices or units, and may be in electrical, mechanical or other forms.

The units described as separate components may or may not be physically separated. The components displayed as units may or may not be physical units, that is, they may be located in one place, or they may be distributed on multiple network units. Some or all of the units may be selected according to actual needs to achieve the objectives of the solutions of the embodiments.

In addition, the functional units in the embodiments of the present disclosure may be integrated into one unit. Alternatively, the units may exist alone physically. Alternatively, two or more units may be integrated into one unit. The integrated unit may be implemented in the form of hardware or software functional unit.

In the case that the integrated unit is implemented in the form of a software functional unit and sold or used as an independent product, it may be stored in a computer readable storage medium. Based on this understanding, the essential part or the part that contributes to the existing technology or all or part of the technical solutions of the present disclosure may be embodied in the form of a software product. The software product may be stored in a storage medium, and may include multiple instructions which may be used to make a computer device (which may be a personal computer, a server, or a network device, etc.) to execute all or part of the steps of the method described in the embodiments of the present disclosure. The storage media may include a U disk, a mobile hard disk, a read-only memory (ROM), a random access memory (RAM), a magnetic disk, an optical disk or other media that can store program code.

The embodiments above are only used to illustrate, but not limit, the technical solutions of the present disclosure. Although the present disclosure has been described in detail with reference to the embodiments above, those of ordinary skill in the art should understand that the technical solutions in the embodiments may be modified or some of the technical features may be equivalently replaced. These modifications or replacements will not cause the essence of the corresponding technical solutions to deviate from the spirit and scope of the technical solutions in the embodiments of the present disclosure.

The invention claimed is:

1. An image analysis method based on an ultrasound imaging device, comprising:
   obtaining an image of a first section of a target object;
   generating a first analysis result corresponding to the target object according to the image of the first section, wherein the first analysis result indicates a first grade of disease of the target object;
   obtaining an image of a second section of the target object;
   generating a second analysis result corresponding to the target object according to the image of the second section, wherein the second analysis result indicates a second grade of disease of the target object;
   generating a diagnostic analysis result of the target object by combining the first analysis result and the second analysis result, wherein the diagnostic analysis result indicates a final grade of disease of the target object; and
   displaying the diagnostic analysis result of the target object,
   wherein generating the diagnostic analysis result of the target object by combining the first analysis result and the second analysis result comprises:
   multiplying the first analysis result by a first coefficient to obtain a first result to be processed;
   multiplying the second analysis result by a second coefficient to obtain a second result to be processed; and
   summing the first result to be processed and the second result to be processed to obtain the diagnostic analysis result of the target object.

2. The image analysis method of claim 1, wherein:
   obtaining the image of the first section of the target object comprises:
   receiving an instruction for selecting the image of the first section; and
   in response to the instruction for selecting the image of the first section, obtaining the image of the first section of the target object; and
   obtaining the image of the second section of the target object comprises:

receiving an instruction for selecting the image of the second section; and in response to the instruction for selecting the image of the second section, obtaining the image of the second section of the target object.

3. The image analysis method of claim 1, after obtaining the image of the second section of the target object, further comprising:

obtaining an image of a third section of the target object; and generating a third analysis result corresponding to the target object according to the image of the third section;

wherein generating the diagnostic analysis result of the target object by combining the first analysis result and the second analysis result comprises:

generating the diagnostic analysis result of the target object by combining the first analysis result, the second analysis result and the third analysis result.

4. The image analysis method of claim 2, after receiving the instruction for selecting the image of the second section, further comprising:

receiving an instruction for ending selection; and in response to the instruction for ending selection, ending the selection of the image of the section and generating the diagnostic analysis result of the target object by combining the first analysis result and the second analysis result.

5. The image analysis method of claim 1, after generating the diagnostic analysis result of the target object by combining the first analysis result and the second analysis result, further comprising:

receiving a data review instruction; and in response to the data review instruction, displaying the first analysis result and/or the second analysis result.

6. The image analysis method of claim 1, wherein:

generating the first analysis result corresponding to the target object according to the image of the first section comprises:

performing a computer-aided diagnosis analysis on the image of the first section to obtain the first analysis result corresponding to the target object, wherein the first analysis result indicates the first grade of disease corresponding to the image of the first section; and generating the second analysis result corresponding to the target object according to the image of the second section comprises:

performing a computer-aided diagnosis analysis on the image of the second section to obtain the second analysis result corresponding to the target object, wherein the second analysis result indicates the second grade of disease corresponding to the image of the second section.

7. The image analysis method of claim 6, wherein:

performing the computer-aided diagnosis analysis on the image of the first section to obtain the first analysis result corresponding to the target object comprises:

extracting a lesion feature in the image of the first section;

analyzing a size, a density or a shape of the lesion feature to obtain a first lesion result; and performing a classification processing on the first lesion result to obtain the first analysis result; and performing the computer-aided diagnosis analysis on the image of the second section to obtain the second analysis result corresponding to the target object comprises:

extracting a lesion feature in the image of the second section;

analyzing a size, a density or a shape of the lesion feature to obtain a second lesion result; and performing a classification processing on the second lesion result to obtain the second analysis result.

8. The image analysis method of claim 1, wherein:

generating the first analysis result corresponding to the target object according to the image of the first section comprises:

receiving a first result analysis instruction; and in response to the first result analysis instruction, generating the first analysis result corresponding to the target object according to the image of the first section; and generating the second analysis result corresponding to the target object according to the image of the second section comprises:

receiving a second result analysis instruction; and in response to the second result analysis instruction, generating the second analysis result corresponding to the target object according to the image of the second section.

9. An image analysis method based on an ultrasound imaging device, comprising:

obtaining a three-dimensional data of a target object;

determining an image of a first section and an image of a second section of the target object according to the three-dimensional data of the target object;

generating a first analysis result corresponding to the target object according to the image of the first section, wherein the first analysis result indicates a first grade of disease of the target object, and generating a second analysis result corresponding to the target object according to the image of the second section, wherein the second analysis result indicates a second grade of disease of the target object;

generating a diagnostic analysis result of the target object by combining the first analysis result and the second analysis result, wherein the diagnostic analysis result indicates a final grade of disease of the target object; and displaying the diagnostic analysis result of the target object, wherein generating the diagnostic analysis result of the target object by combining the first analysis result and the second analysis result comprises:

multiplying the first analysis result by a first coefficient to obtain a first result to be processed;

multiplying the second analysis result by a second coefficient to obtain a second result to be processed; and summing the first result to be processed and the second result to be processed to obtain the diagnostic analysis result of the target object.

10. The image analysis method of claim 9, after determining the image of the first section and the image of the second section of the target object according to the three-dimensional data of the target object, further comprising:

determining an image of a third section of the target object according to the three-dimensional data of the target object; and generating a third analysis result corresponding to the target object according to the image of the third section;

wherein generating the diagnostic analysis result of the target object by combining the first analysis result and the second analysis result comprises:

generating the diagnostic analysis result of the target object by combining the first analysis result, the second analysis result and the third analysis result.

11. The image analysis method of claim 9, wherein generating the diagnostic analysis result of the target object by combining the first analysis result and the second analysis result comprises:
- receiving a result analysis instruction; and
- in response to the result analysis instruction, generating the diagnostic analysis result of the target object by combining the first analysis result and the second analysis result.

12. The image analysis method of claim 9, after determining the image of the first section and the image of the second section of the target object according to the three-dimensional data of the target object, further comprising:
- receiving an image display instruction; and
- in response to the image display instruction, enlarging and displaying the image of the first section and/or the image of the second section.

13. An image analysis method based on an ultrasound imaging device, comprising:
- transmitting ultrasound waves to a target object;
- receiving ultrasound echoes of the ultrasound waves returned from the target object to obtain ultrasound echo signals;
- generating images of at least two sections of the target object according to the ultrasound echo signals, comprising:
  - obtaining an image of a first section of the target object;
  - generating a first analysis result corresponding to the target object according to the image of the first section, wherein the first analysis result indicates a first grade of disease of the target object;
  - obtaining an image of a second section of the target object; and
  - generating a second analysis result corresponding to the target object according to the image of the second section, wherein the second analysis result indicates a second grade of disease of the target object; and
- generating a diagnostic analysis result of the target object by combining the first analysis result and the second analysis result, wherein the diagnostic analysis result indicates a final grade of disease of the target object,
- wherein generating the diagnostic analysis result of the target object by combining the first analysis result and the second analysis result comprises:
- multiplying the first analysis result by a first coefficient to obtain a first result to be processed;
- multiplying the second analysis result by a second coefficient to obtain a second result to be processed; and
- summing the first result to be processed and the second result to be processed to obtain the diagnostic analysis result of the target object.

* * * * *